(12) United States Patent
Bancaud et al.

(10) Patent No.: US 10,107,781 B2
(45) Date of Patent: Oct. 23, 2018

(54) METHOD FOR SEPARATING BIOLOGICAL MOLECULES AND CELLS IN SOLUTION

(71) Applicant: CENTRE NATIONAL DE LA RECHERCHE SCIENTIFIQUE, Paris (FR)

(72) Inventors: Aurélien Bancaud, Toulouse (FR); Hubert Ranchon, Toulouse (FR)

(73) Assignee: CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 219 days.

(21) Appl. No.: 14/417,063

(22) PCT Filed: Jul. 29, 2013

(86) PCT No.: PCT/FR2013/051821
§ 371 (c)(1),
(2) Date: Jan. 23, 2015

(87) PCT Pub. No.: WO2014/020271
PCT Pub. Date: Feb. 6, 2014

(65) Prior Publication Data
US 2015/0204816 A1    Jul. 23, 2015

(30) Foreign Application Priority Data
Aug. 3, 2012 (FR) ...................................... 12 57587

(51) Int. Cl.
*G01N 27/447* (2006.01)
(52) U.S. Cl.
CPC . *G01N 27/44791* (2013.01); *G01N 27/44765* (2013.01)
(58) Field of Classification Search
CPC ....................... G01N 27/44791; G01N 27/447
See application file for complete search history.

(56) References Cited

U.S. PATENT DOCUMENTS 5,552,028 A * 9/1996 Madabhushi .... G01N 27/44752
204/451
2003/0230486 A1* 12/2003 Chien ................. B01F 13/0076
204/450

(Continued)

FOREIGN PATENT DOCUMENTS

WO    WO 2004/103566 A1    12/2004

OTHER PUBLICATIONS

Afonso et al., "Analytical solution of mixed electro-osmotic/pressure driven flows of viscoelastic fluids in microchannels", Journal of Non-Newtonian Fluid Mechanics, vol. 159, pp. 50-63, 2009.

(Continued)

*Primary Examiner* — Susan D Leong
(74) *Attorney, Agent, or Firm* — Birch, Stewart, Kolasch & Birch, LLP (57) ABSTRACT

A method for separating a plurality of deformable objects, such as biological cells or biological supramolecules such as DNA, in a liquid medium by use of an electrophoretic technique combined with hydrodynamic forces. The deformable objects are introduced into a channel, having a flow axis and a cross section at right angles to the flow axis, with the minimum size of the cross section being less than or equal to 50 pm; A hydrodynamic flow is defined a in the channel together with the application of an electric field in the channel, making it possible to move the deformable objects in the channel according to the flow axis and to separate them along the flow axis. A device suitable for implementing this method. The electrolyte used for the electrophoretic separation may be a non-Newtonian fluid with viscoelastic properties.

8 Claims, 6 Drawing Sheets

(56) References Cited

U.S. PATENT DOCUMENTS

| | | | | |
|---|---|---|---|---|
| 2007/0209941 A1* | 9/2007 | Holland | ............ | B01L 3/502738 204/601 |
| 2008/0242556 A1 | 10/2008 | Cao et al. | | |
| 2009/0071828 A1* | 3/2009 | Squires | ............ | B01L 3/502784 204/453 |

OTHER PUBLICATIONS

Davis et al., Capillary and Microfluidic Gradient Elution Isotachophoresis Coupled to Capillary Zone Electrophoresis for Femtomolar Amino Acid Detection Limits, Analytical Chemistry, vol. 81, pp. 5452-5459, 2009.

Viero et al., "Efficient prototyping of large-scale pdms and silicon nanofluidic devices using pdms-based phase-shift lithography", Microfluid Nanofluid, pp. 465-473, 2012.

Wu et al., "Microfluidic continuous particle/cell separation via electroosmotic-flow-tuned hydrodynamic spreading", Journal of Micromechanics and Microengineering, vol. 17, pp. 1992-1997, 2007.

B. Rogers, et al., "Bundled Capillary Electrophoresis Using Microstructured Fibres," Electrophoresis 2011, Department of Chemistry 32,Queen's University, Kingstron, OH, Canada, pp. 223-229.

J. Zheng, et al., "Mechanism for the Separation of Large Molecules Based on Radial Migration in Capillary Electrophoresis," Analytical Chemistry, vol. 75, No. 15, Aug. 1, 2003, pp. 3675-3680.

K. Liu, et al., "Single Molecule Analysis Enables Free Solution Hydrodynamic Separation Using Yoctomole Levels of DNA," Journal of American Chemical Soc., May 11, 2011, (10 pages).

M. Unger, et al., "Monolithic Microfabricated Valves and Pumps by Multilayer Soft Lithography," Science 288, (2000); Apr. 7, 2000, pp. 113-116.

S. Pennathur, et al., "Free-Solution Oligonucleotide Separation in Nanoscale Channels," Analytical Chemistry, vol. 79, No. 21, Nov. 1, 2007 (pp. 8316-8322).

X. Wang, et al., "Resolving DNA in Free Solution," Trends in Analytical Chemistry, vol. 35, 2012, pp. 122-134.

* cited by examiner

METHOD FOR SEPARATING BIOLOGICAL MOLECULES AND CELLS IN SOLUTION

FIELD OF THE INVENTION

The present invention relates to a method for separating molecules and deformable objects in solution, and to a device capable of carrying out this method.

TECHNICAL BACKGROUND

Methods for separating biomolecules, such as nucleic acids and proteins, by size are fundamental to research and diagnostic activities.

Conventionally, separation is carried out by electrophoresis, that is to say by displacement of the molecules under the effect of an electric field. Electrophoresis is conventionally carried out in a matrix, which can be a gel or a polymer solution.

However, conventional gel electrophoresis requires large quantities of material, is of long duration and has a limited resolution for large molecule sizes (for example for DNA molecules of more than 40 or 50 kb). The use of a pulsed field allows the resolution power for molecules of large size to be improved, but it is carried out over an even longer duration (greater than 10 hours).

Electrophoresis carried out in capillary tubes is more rapid and more effective than conventional gel electrophoresis. However, the introduction of matrices into the capillary tubes is problematic. The cross-linking of gels in situ is difficult to reproduce, and the use of polymer solutions of high viscosity requires the application of a very high pressure for filling and emptying the tubes.

It is therefore desirable to have available methods for separating biomolecules by size which do not use separating matrices.

The article entitled "*Mechanism for the separation of large molecules based on radial migration in capillary electrophoresis*" by Zheng & Yeung in *Anal. Chem.* 75:3675-3680 (2003) describes a technique for separating DNA in a capillary tube having an inside diameter of 75 µm without a separating matrix, based on the phenomenon of radial migration. This phenomenon consists in displacing the DNA molecules either towards the centre of the capillary or towards its periphery, by joint application of a hydrodynamic flow and an electric field, as a function of the relative direction of the hydrodynamic flow and of the electric field. The authors state that the speed of radial migration depends on the size of the molecules. Accordingly, they propose a separation by size of two molecules of approximately 48 kb and 5 kb by electrophoresis combined with the cyclic application of a hydrodynamic flow of alternating direction. The use of a constant electric field and a constant hydrodynamic flow, on the other hand, does not permit a satisfactory resolution.

The article entitled "*Single molecule analysis enables free solution hydrodynamic separation using yoctomole levels of DNA*" by Liu et al. in *J. Am. Chem. Soc.* 133:6898-6901 (2011) describes a separation of DNA molecules by size in a solution without a matrix, inside a capillary tube having an inside diameter of 2 µm, which is of purely hydrodynamic type.

The article "*Free-solution oligonucleotide separation in nanoscale channels*" by Pennathur et al. in *Anal. Chem.* 79:8316-8322 (2007) describes a method of separating DNA molecules of small size (10 to 100 bp) in nanochannels, under the effect of an electric field and without a separating matrix. The authors explain that the migration of the molecules depends especially on the interactions thereof with the electrical double layer, on the steric hindrance and on the presence of end labelling with a fluorescein group (which alters the electrophoretic mobility of the molecules of small size).

The review "*Resolving DNA in free solution*" by Wang et al. in *Trends in Analytical Chemistry*, 35:122-134 (2012) describes a number of approaches for separating DNA by size without a matrix. In addition to the technique of Zheng & Yeung mentioned above, the review describes techniques of electrophoresis with end labelling of the molecules (which requires a charge to be attached to the DNA molecules at their ends), of entropic trapping, of DNA prism, etc.

However, all the above methods have the disadvantage of requiring a relatively long separation time, sometimes the use of very low, unconventional saline concentrations, and more generally of being complex to carry out and having insufficient resolution over a broad molecule size range.

There is therefore a need to develop a method for separating molecules or other objects without a separating matrix, which method requires a shorter separation time and is more simple and flexible to carry out than the methods of the prior art.

SUMMARY OF THE INVENTION

The invention relates in the first instance to a method for separating a plurality of molecules or deformable objects in a liquid medium, comprising:
  introducing the molecules or deformable objects into a channel, the channel having a flow axis and a cross section orthogonal to the flow axis, and the minimum dimension of said cross section being less than or equal to 25 µm; and
  applying a hydrodynamic flow in the channel together with the application of an electric field in the channel, allowing the molecules or deformable objects to be displaced in the channel according to the flow axis and to be separated along the flow axis.

"Deformable objects" are understood as being molecules or other more complex objects, such as supramolecular assemblies or cells or fragments of cells, which are capable of being deformed under the effect of a mechanical stress such as a hydrodynamic flow. Preferably, the deformability is measured by the Young's modulus of the object, which must be less than or equal to $10^9$ Pa or, according to embodiments, less than or equal to $10^8$ Pa, or $10^7$ Pa, or $10^6$ Pa, or $10^5$ Pa, or $10^4$ Pa, or $10^3$ Pa.

The Young's modulus can be measured by mechanical contact, for example by atomic force microscopy.

By way of example, the Young's modulus of DNA is typically approximately 300 MPa; that of mammalian cells is approximately from 0.1 to 100 kPa.

Within the scope of the present application, deformable objects are considered as being especially: DNA or RNA molecules having at least 100 bases or base pairs (for example at least 1000); peptides, polypeptides or proteins having at least 100 amino acid units (for example at least 200); and cells.

According to one embodiment, the introduction of the molecules or deformable objects is carried out in an introduction zone of the channel, and the displacement of the molecules or deformable objects is carried out from the introduction zone to a detection zone of the channel, the method further comprising:

detecting molecules or deformable objects which arrive in the detection zone.

According to one embodiment:

the minimum dimension of the channel is less than or equal to 15 µm, or less than or equal to 10 µm, or less than or equal to 5 µm, or less than or equal to 2 µm; and/or the ratio between the minimum dimension of the cross section and the dimension of the cross section in a direction orthogonal to that of the minimum dimension is less than or equal to 1/10, preferably less than or equal to 1/15, more particularly preferably less than or equal to 1/20; and/or the distance between the introduction zone and the detection zone of the channel is from 500 µm to 20 cm, preferably from 1 mm to 10 cm, and more particularly preferably from 2 mm to 1 cm.

According to one embodiment, the molecules are chosen from nucleic acid molecules, and especially single-stranded DNA, double-stranded DNA and RNA molecules, peptides, polypeptides or proteins, other polymers, carbohydrates, lipids, metabolites and pharmaceutical compounds. The molecules are preferably polymers.

According to one embodiment, the deformable objects are chosen from molecules and cells; the molecules preferably being chosen from nucleic acid molecules, and especially single-stranded DNA, double-stranded DNA and RNA molecules, peptides, polypeptides or proteins, polymeric carbohydrates and other polymers.

According to one embodiment:

the electric field applied is from 10 V/m to 10,000 V/m, preferably from 100 V/m to 5000 V/m, and more particularly preferably from 200 V/m to 1000 V/m; and/or the hydrodynamic flow in the channel, and especially between the introduction zone and the detection zone, is characterised by an average speed of from 1 to 10,000 µm/s, preferably from 5 to 5000 µm/s, and more particularly preferably from 10 to 1000 µm/s.

According to one embodiment, the liquid medium used for the separation is a non-Newtonian fluid.

"Newtonian fluid" is understood as meaning a fluid in which there is a linear relationship between the imposed mechanical stress (force exerted on the fluid per unit area) and the shear of the fluid (that is to say a velocity gradient of the fluid). A "non-Newtonian fluid" is therefore a fluid which is not a Newtonian fluid.

For example, a non-Newtonian fluid according to the invention can have a viscosity coefficient dependent on the shear (stationary fluid); or it can have elastic behaviour. According to one embodiment, the fluid is viscoelastic. According to one embodiment, the fluid has a shear storage modulus $G'(w)$ (as defined in the examples section) which increases with the frequency $\omega$ of a vibration to which the fluid is subjected. According to one embodiment, the fluid has a shear storage modulus $G'(w)$ greater than the shear loss modulus $G''(w)$ (as defined in the examples section) for frequencies $w$ of vibration greater than a threshold $w_0$. The threshold $w_0$ can be, for example, between 0.01 Hz and 10,000 Hz, especially between 0.1 Hz and 1000 Hz, and by way of illustration between 1 Hz and 100 Hz.

According to one embodiment, the liquid medium has a viscosity of from 1 to 100 cP (centipoise), preferably from 2 to 20 cP, and yet more preferably from 2 to 10 cP at an ambient temperature. Unless mentioned otherwise, the viscosity values mentioned in the application are static viscosity values.

According to one embodiment, the liquid medium comprises uncharged polymers, preferably chosen from polyvinylpyrrolidone, poly(ethylene glycol), polyacrylamide and mixtures thereof.

The term "uncharged" means that the polymers in question have a total electrostatic charge of substantially zero in the above-mentioned liquid medium.

The presence of such polymers, for example, in an aqueous solution allows the liquid medium to be rendered non-Newtonian (for example viscoelastic).

According to one embodiment, the uncharged polymers are present in a concentration by mass of from 0.1 to 10%, preferably from 0.5 to 5%, more particularly preferably from 1 to 4%.

Preferably, the concentration of uncharged polymers is greater than or equal to the critical coverage concentration (concentration from which the polymers are in contact).

According to one embodiment, the uncharged polymers have an average molecular mass (by mass) of from 10 to 100,000 kDa, preferably from 50 to 10,000 kDa, more particularly preferably from 100 to 1000 kDa.

The invention also relates to a device for separating molecules or deformable objects in a liquid medium, comprising:

a channel having a flow axis and a cross section orthogonal to the flow axis, the minimum dimension of said cross section being less than or equal to 25 µm;

means for applying a hydrodynamic flow in the channel; and means for applying an electric field in the channel.

Preferably, the channel is filled with a non-Newtonian liquid medium.

According to one embodiment, the liquid medium has a viscosity of from 1 to 100 cP, preferably from 2 to 20 cP, and yet more preferably from 2 to 10 cP at an ambient temperature.

According to one embodiment, the liquid medium comprises uncharged polymers, preferably chosen from polyvinylpyrrolidone, poly(ethylene glycol), polyacrylamide and mixtures thereof.

According to one embodiment, the uncharged polymers are present in a concentration by mass of from 0.1 to 10%, preferably from 0.5 to 5%, more particularly preferably from 1 to 4%.

According to one embodiment, the uncharged polymers have a mean molecular mass (by mass) of from 10 to 100,000 kDa, preferably from 50 to 10,000 kDa, more particularly preferably from 100 to 1000 kDa.

According to one embodiment, the device comprises:

a plurality of channels (1) each having a flow axis (14) and a cross section orthogonal to the flow axis (14), the minimum dimension of said cross section being less than or equal to 25 µm and each channel (1) being filled with a non-Newtonian liquid medium;

means for applying a hydrodynamic flow (13a, 13b) in the channels (1); and means for applying an electric field (10a, 10b) in the channels (1).

According to one embodiment, the channel is a lumen of a capillary tube; or the plurality of channels are lumens of capillary tubes, preferably arranged in parallel.

According to one embodiment, the device comprises:

an introduction zone and a detection zone in the channel, which zones are spaced along the flow axis;

means for detecting molecules or deformable objects which arrive in the detection zone.

According to one embodiment:
the minimum dimension of the channel is less than or equal to 15 or less than or equal to 10 µm, or less than or equal to 5 µm, or less than or equal to 2 µm; and/or
the ratio between the minimum dimension of the cross section and the dimension of the cross section in a direction orthogonal to that of the minimum dimension is less than or equal to $1/10$, preferably less than or equal to $1/15$, more particularly preferably less than or equal to $1/20$; and/or
the distance between the introduction zone and the detection zone of the channel is from 500 µm to 20 cm, preferably from 1 mm to 10 cm, and more particularly preferably from 2 mm to 5 cm or from 2 mm to 1 cm.

According to one embodiment, the introduction zone of the channel is formed by an intersection of the channel with an additional channel, the device comprising means for bringing the molecules or deformable objects into the additional channel, and means for displacing the molecules or deformable objects towards the intersection, which preferably comprise means for applying an electric field in the additional channel and/or means for applying a hydrodynamic flow in the additional channel.

The invention also relates to a lab-on-a-chip system comprising the separating device described above, connected at the outlet of a chemical or biochemical reaction device and/or supplying means for collecting the separated molecules or deformable objects.

The present invention makes it possible to overcome the disadvantages of the prior art. More particularly, it provides a method for separating molecules and other deformable objects without a separating matrix, which method requires a shorter separation time and is more simple and flexible to carry out than the methods of the prior art.

This is achieved by virtue of the application of an electric field together with the application of a hydrodynamic flow, in a channel of small dimension, especially less than 25 µm.

By adjusting the value of the electric field and the average speed of the fluid (and optionally the dimensions of the channel), these conditions allow molecules and other deformable objects in very varied size ranges to be separated with good resolution and in a short time.

Without wishing to be bound by one theory, the inventors think that the separation of molecules or other deformable objects carried out in the invention is based on the combined action on the molecules or objects of an electrostatic force and a shear force, resulting in a different distribution of the molecules or objects according to the smallest dimension of the channel as a function of their respective sizes, and therefore in a displacement speed of these molecules or objects in the channel that is dependent on their respective sizes—the molecules or objects in a relatively central position being subjected to a greater flow speed than the molecules or objects in a relatively off-centred position. More specifically, it has been observed that molecules of small size move to the detection zone more rapidly than do molecules of large size, owing to the fact that the molecules of large size have a more off-centred position than the molecules of small size according to the smallest dimension of the channel.

Without wishing to be bound by one theory, the inventors further think that, when the liquid medium in the channel is non-Newtonian, the separation of the molecules or other deformable objects is improved by facilitating the transverse migration of the molecules or objects that is dependent on the shear to which they are subjected. Apart from the main features of the invention set out above, the method and the device according to the invention can additionally have one or more of the other features which follow. According to one embodiment, the molecules or deformable objects to be separated are molecules or deformable objects having a positive overall charge in the liquid medium used for the separation.

According to one embodiment, the molecules or deformable objects to be separated are molecules or deformable objects having a negative overall charge in the liquid medium used for the separation.

According to one embodiment, the molecules or deformable objects to be separated have identical (or substantially identical, for example to within about 5, 10 or 20%) electrophoretic mobility in the liquid medium used for the separation.

According to one embodiment, the electric field, the hydrodynamic flow and the composition of the liquid separation medium are selected and adapted so as to effect heterogeneous distribution of the molecules or deformable objects in the cross section of the channel, and especially in the direction of that cross section corresponding to the minimum dimension; and more particularly are selected and adapted so that the concentration of molecules or deformable objects decreases from the walls of the channel to the centre of the channel, in the direction corresponding to the minimum dimension of the cross section of the channel.

According to one embodiment, the molecules or deformable objects to be separated are biomolecules.

The molecules or deformable objects subjected to the method of the invention generally comprise a plurality of (that is to say at least two) different types of molecules or deformable objects, it being possible for each type of molecules or deformable objects to include a single molecule/deformable object or, preferably, a plurality (and especially a large number) of molecules/deformable objects. The invention allows the molecules to be separated according to those types of molecules, or the deformable objects to be separated according to those types of deformable objects.

"Type of molecules" is understood as meaning especially molecules having a molecular weight or size which is identical or similar (which belongs especially to a range of values which is defined and distinct from that of the molecular weight or size of another type of molecules).

In particular, when the molecules are polymers (such as nucleic acids or peptides, polypeptides or proteins, for example), "type of molecules" is generally understood as meaning one of those polymers having a size (that is to say a number of monomer units, such as number of bases, base pairs, or amino acids) which is given or is within a given range. In this case, the different types of molecules therefore correspond to distinct sizes (or size ranges).

"Type of deformable objects", in the context of cells, is understood especially as meaning cells having mobility under the action of an electric field (or a surface charge density) or a size which is identical or similar (which belongs especially to a range of values which is defined and distinct from that of the mobility or size of another type of cells).

Accordingly, when the deformable objects are cells (such as fibroblasts, osteoblasts, endothelial or epithelial cells, for example), "type of cells" is generally understood as meaning cells having equal or similar deformability properties.

According to one embodiment, the electric field and the hydrodynamic flow are constant during the displacement of the molecules or deformable objects from the introduction zone to the detection zone. This embodiment is particularly simple to carry out. Alternatively, it is possible to vary the hydrodynamic flow and/or the electric field during the displacement of the molecules or deformable objects, for example in a cyclic manner. This can make it possible to define a refined programme which is particularly adapted to certain types of molecules or deformable objects which are to be separated.

According to one embodiment, the liquid medium present in the channel is a solution without a separating matrix. In particular, no gel is then used, and no polymer is present in the liquid medium—with the exception, where appropriate, of the polymeric molecules on which the separation is to be carried out or other polymers having auxiliary functions (for example passivation of surfaces, screening of hydrodynamic interactions, polymers such as polyvinylpyrrolidone or others which impart a desired non-Newtonian character to the liquid medium, etc.).

A separating matrix is in fact a medium such as a gel or a polymer solution which allows an electrophoretic separation to be carried out without setting said matrix in motion during the separation operation, and under the effect solely of an electric field.

According to one embodiment, the method of the invention comprises a step of injecting the molecules or deformable objects into a separating device comprising the channel mentioned above. Preferably, the injection step comprises injecting a liquid sample having a volume less than or equal to 1 ml, or 500 µl, or 300 µl, or 200 µl, or 150 µl.

According to one embodiment, the concentration of the molecules or deformable objects in the channel is from $10^{-18}$ to $10^{-8}$ mol/µl, or from $10^{-18}$ to $10^{-10}$ mol/µl, or from $10^{-17}$ to $10^{-12}$ mol/µl, or from $10^{-16}$ to $10^{-14}$ mol/µl.

According to one embodiment, the walls of the channel have a coating adapted to reduce or prevent interactions between the molecules or deformable objects which are to be separated and these walls. This coating can be chemically grafted onto the walls or provided by the solutions that are introduced. Preferably, the coating is chosen from synthetic polymers such as polyvinylpyrrolidone, poly(ethylene glycol), polyacrylamide, or biological polymers such as bovine or egg albumin.

Accordingly, the method of the invention can comprise a preliminary step of injecting into the channel a solution for forming a coating on the walls of the channel, followed by a step of rinsing the channel.

Alternatively, the polymers providing the coating can be included directly in the liquid medium containing the molecules or objects to be separated.

In other words, when a liquid medium comprising uncharged polymers is used for carrying out the separation, as mentioned above, these uncharged polymers can also perform the function of preventing interactions between the molecules or objects which are to be separated and the walls.

The detection of the molecules or deformable objects in the detection zone can be carried out especially by:
  illuminating the detection zone and detecting a fluorescence signal by means of a photodetector; or
  illuminating the detection zone and detecting an absorbance signal at a specific wavelength of the molecule of interest or of the object of interest (for example 280 nm for proteins, 260 nm for DNA); or
  electrochemical probe placed in the detection zone, and detecting an impedance variation by means of an electrical detector; or
  detecting an optical signal variation associated with the passage of objects in front of the detection zone, by means of a photodetector.

Where appropriate, the method according to the invention comprises a preliminary step of bringing the molecules or deformable objects into contact with a colouring agent such as a fluorophore.

According to one embodiment, the method according to the invention comprises detecting individual molecules or individual deformable objects in the detection zone (for example by means of a photodetector) at different times. Alternatively (or conjointly), the method according to the invention comprises measuring a concentration of molecules or deformable objects in the detection zone at different times.

According to one embodiment, the hydrodynamic flow is of a laminar type.

According to one embodiment, the electric field in the channel tends to oppose the displacement of the molecules or deformable objects.

According to one embodiment, the channel does not have structuring on its inside walls.

According to one embodiment, the cross section of the channel is constant along the flow axis, and preferably the cross section of the channel is substantially rectangular.

According to one embodiment, the channel is straight according to the flow axis. Alternatively, the channel can include straight sections connected by bends, in which case the flow axis is substantially a broken line. Alternatively, the channel can be curved according to the flow axis: for example, the flow axis can be an arc of a circle, a portion of a spiral, etc.

According to some variants, the channel can include one or more branches.

According to one embodiment, the minimum dimension of the cross section mentioned above is the height of the channel (according to the vertical dimension).

According to one embodiment, the height of the channel is less than or equal to 25 µm, or 20 µm, or 15 µm, or 10 µm, or 8 µm, or 7 µm, or 6 µm, or 5 µm, or 4 µm, or 3 µm, or 2 µm, or 1 µm, or 800 nm.

According to one embodiment, the dimension of the cross section in an orthogonal direction is the width of the channel.

According to one embodiment, the minimum dimension of the cross section is chosen as a function of the maximum size or of the average size of the molecules or deformable objects to be separated in the liquid medium.

According to one embodiment, that minimum dimension is greater than or equal to 100 nm, or 200 nm, or 300 nm, or 500 nm. Preferably, the separation method according to the invention is thus not based on significant charge effects in the region of the walls.

According to one embodiment, that minimum dimension is less than or equal to 200 times, preferably less than or equal to 100 times, or 50 times, or 20 times: the maximum dimension in solution of the type of molecules or deformable objects which are the largest among the molecules or deformable objects to be separated; or the average of the maximum dimension in solution of the type of molecules or deformable objects which are the largest among the molecules or deformable objects to be separated, and the maximum dimension in solution of the type of molecules or deformable objects which are the smallest among the molecules or deformable objects to be separated.

According to one embodiment, that minimum dimension is less than or equal to 200 times, preferably less than or equal to 100 times, or 50 times, or 20 times: the radius of gyration of the type of molecules which are the largest among the molecules to be separated; or the average of the radius of gyration of the type of molecules which are the largest among the molecules to be separated and the radius of gyration of the type of molecules which are the smallest among the molecules to be separated. The radius of gyration provides an estimate of the maximum dimension of a molecule in solution, when it has a coil-type conformation.

For example, for double-stranded DNA molecules having a size greater than or equal to several kb, in a good solvent, the radius of gyration is $A_0 \times N^v$, where N is the number of base pairs, $A_0$ is a characteristic length and v is an exponent dependent on the nature of the solvent (approximately ⅓ for a poor solvent, and from 0.5 to 0.6 for a good solvent).

For proteins, the radius of gyration or hydrodynamic radius is generally considered to be approximately $0.75 \times M^{0.33}$ for globular proteins and $0.19 \times M^{0.54}$ for denatured proteins, in nm, where M denotes the molecular weight.

According to one embodiment, in the case of the separation of cells, the minimum dimension is less than or equal to 200 times, preferably less than or equal to 100 times, or 50 times, or 20 times the average diameter of the type of cells which are the largest among the cells to be separated; or the average of the average diameter of the type of cells which are the largest among the cells to be separated, and the average diameter of the type of cells which are the smallest among the cells to be separated. In the case of anisotropic cells, the average diameter denotes the average value of the maximum dimension of the cells.

According to one embodiment, some of the molecules or deformable objects to be separated, or all of the molecules or deformable objects to be separated, are nucleic acid molecules:
- comprising a number of bases (or base pairs) of less than or equal to 100; or
- comprising a number of bases (or base pairs) in a range of from 100 to 1000; or
- comprising a number of bases (or base pairs) in a range of from 1000 to 10,000; or
- comprising a number of bases (or base pairs) in a range of from 10,000 to 100,000; or
- comprising a number of bases (or base pairs) in a range of from 100,000 to 1,000,000; or
- comprising a number of bases (or base pairs) in a range of from 2,000,000 to 10,000,000; or
- comprising a number of bases (or base pairs) in a range of from 10,000,000 to 100,000,000.

According to one embodiment, the molecules or deformable objects to be separated are nucleic acid molecules comprising more than 1000 bases (or base pairs) or more than 10,000 bases (or base pairs).

According to one embodiment, the molecules or deformable objects to be separated are genomic nucleic acid molecules. Preferably, in this case, the minimum dimension of the cross section of the channel is from 5 to 25 µm, especially from 5 to 20 µm, preferably from 10 to 15 µm.

According to one embodiment, the molecules or deformable objects to be separated are nucleic acid molecules comprising not more than 50,000 bases (or base pairs). Preferably, in this case, the minimum dimension of the cross section of the channel is less than or equal to 5 µm, especially less than or equal to 3 µm or less than or equal to 2 µm.

According to one embodiment, the molecules or deformable objects to be separated are proteins. Preferably, in this case, the minimum dimension of the cross section of the channel is less than or equal to 1 µm and is especially from 500 nm to 1 µm, for example from 600 nm to 800 nm.

According to one embodiment, the means for applying the hydrodynamic flow in the channel comprise two liquid reservoirs arranged at the respective ends of the channel relative to the flow axis, said reservoirs being connected to pressure control means.

By way of example, it is possible to use the pressure control means described in document WO 2004/103566, the content of which is incorporated by reference.

Alternatively, a system of valves and pumps as described in the article "*Monolithic Microfabricated Valves and Pumps by Multilayer Soft Lithography*" by Unger et al. in Science (2000), vol. 288, no. 5463, pp. 113-116 can be used.

According to one embodiment, the means for applying the electric field in the channel comprise two electrodes arranged at the respective ends of the channel relative to the flow axis.

According to one embodiment, the means for applying the hydrodynamic flow in the additional channel comprise two liquid reservoirs arranged at the respective ends of the additional channel, said reservoirs being connected to pressure control means.

According to one embodiment, the means for applying the electric field in the additional channel comprise two electrodes arranged at the respective ends of the additional channel.

According to one embodiment, the channel is integrated into a microfabricated chip sealed on a support. Preferably, the support is transparent. The support can especially be a glass slide. The microfabricated chip can especially be made of glass or silicon, or of any other substantially non-deformable material (for example plastics material). The expression "substantially non-deformable" relates to the pressure conditions normally used for the application of the hydrodynamic flow. For example, a reference pressure for non-deformability can be 10 bar.

Alternatively, the channel can be a lumen of a capillary tube. In this case, the cross section of the channel is preferably circular or square, and the minimum dimension of the cross section corresponds to the diameter of the circular section or to the dimension of one side of the square section, respectively.

The use of capillary tubes can permit easy multiplexing of the channels according to the invention, in the form of bundles of capillary tubes, for example such as those described in the article "*Bundled capillary electrophoresis using microstructured fibres*" by Rogers et al., *Electrophoresis*, 32(2):223-229 (2011). In this case, the means for applying the hydrodynamic flow and the means for applying the electric field can be common to all the capillary tubes, or on the other hand can be separate for all the capillary tubes.

According to an alternative form of the invention, the minimum dimension of the cross section of the channel is less than or equal to 200 µm, or 100 µm, or 75 µm, or 50 µm, instead of being less than or equal to 25 µm as mentioned above. The whole of the present description applies to this alternative form of the invention mutatis mutandis, it being understood that the expression "minimum dimension of the cross section less than or equal to 25 µm" must then be replaced by the reader with "minimum dimension of the cross section less than or equal to 200 µm" (or 100 µm, or 75 µm, or 50 µm, according to the variant under consideration).

This alternative form is particularly appropriate when the deformable objects to be separated are of large size, for example are cells. Preferably, in this case, the minimum dimension of the cross section of the channel is less than or equal to 100 and is especially from 10 to and especially from 25 to 50 µm.

This alternative form is also appropriate when the liquid medium used is of high viscosity (in order to facilitate the application of the hydrodynamic flow, that is to say to reduce the necessary pressure difference).

Another object of the invention is a set (or kit) comprising deformable objects (as described above) in association with a device for separating said deformable objects in a liquid medium, the separating device being the device described above (in its different variants and embodiments). The separating device of this set can comprise the liquid medium (suitable for the separation) in the channel or channels; or it can be empty (without liquid medium in the channel or channels) and simply be intended to receive this liquid medium (which is preferably non-Newtonian).

Another object of the invention is a set (or kit) comprising a device for separating deformable objects in a liquid medium, in association with a liquid medium suitable for separating the deformable objects. The separating device is as described above (in its different variants and embodiments); in this set, the device is provided empty (that is to say without the liquid separation medium). The liquid medium is as described above (in its different variants and embodiments) and can especially be non-Newtonian.

Another object of the invention is the use of a device for separating deformable objects in a liquid medium, the device comprising:
  a channel having a flow axis and a cross section orthogonal to the flow axis, the minimum dimension of said cross section being less than or equal to 25 µm;
  means for applying a hydrodynamic flow in the channel; and
  means for applying an electric field in the channel.

According to embodiments of this other object of the invention, the deformable objects have the features described above in relation to the preceding objects of the invention; and/or the separating device has the features described above in relation to the preceding objects of the invention; and/or the liquid medium has the features described above in relation to the preceding objects of the invention (and especially is non-Newtonian).

BRIEF DESCRIPTION OF THE DRAWINGS

In FIG. 10, the components of the complex modulus of elasticity in Pa (G' and G") are shown on the y axis, and the response frequency of the fluid in Hz is shown on the x axis. In FIG. 11, the viscosity in Pa is shown on the y axis, and the shear rate in $s^{-1}$ is shown on the x axis, under steady-state conditions (see example 3).

DESCRIPTION OF EMBODIMENTS OF THE INVENTION

The invention will now be described in greater detail and in a non-limiting manner in the description which follows.

Unless mentioned otherwise, the concentrations indicated in the application are concentrations by mass.

Figure 1:
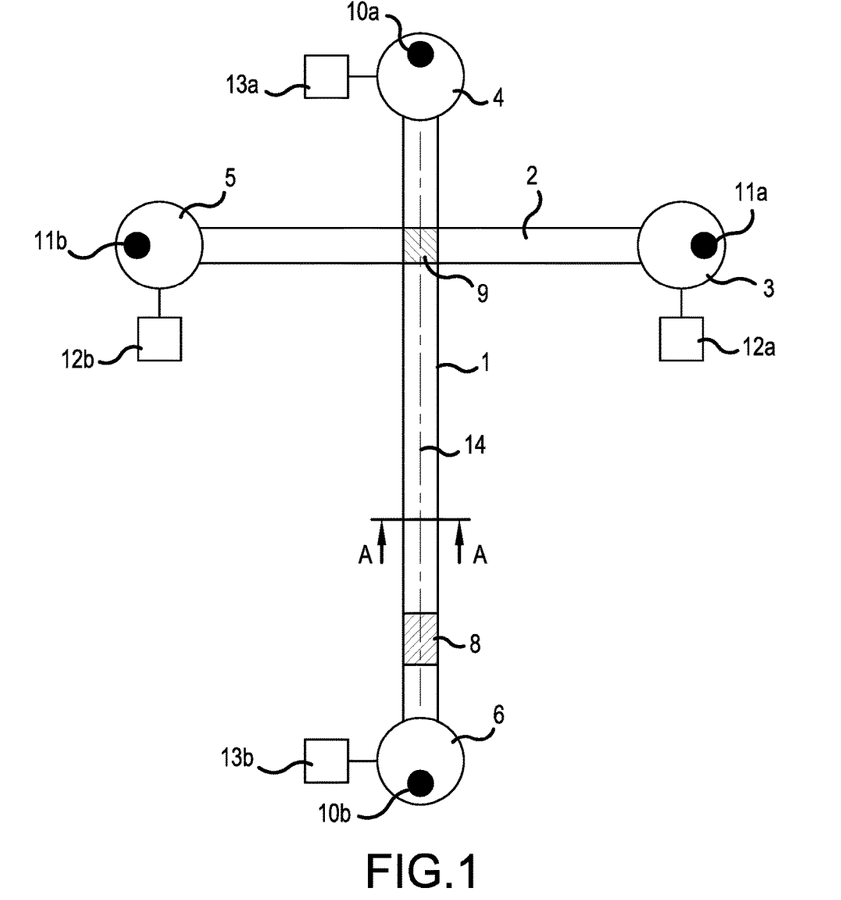
FIG. 1 is a schematic top view of an embodiment of a device according to the invention.
Figure 2:
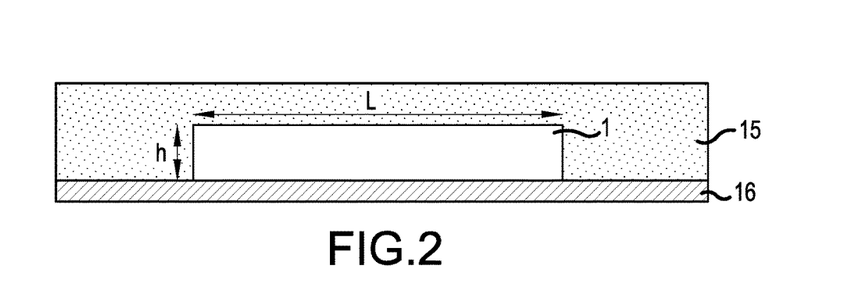
FIG. 2 schematically shows the cross section A-A (enlarged) of the above device.

Referring to FIGS. 1 and 2, the device according to the invention comprises a support 16, which can be a glass slide or plate, and a structure 15 having a recess (for example a microfabricated structure), which can be made of silicon, sealed to the support 16 in a manner known per se. For example, it is possible to use techniques of film deposition, photolithography, etching (chemical or plasma) and adhesive bonding. The film deposition can be carried out by centrifugation, by thermal oxidation, by chemical or physical vapour deposition (CVD and PVD), by low-pressure CVD, by plasma-enhanced CVD, by spraying, etc.

The structure 15 (with its recess) and the support 16 define a channel 1. The channel 1 has the form of a hollow cylinder of rectangular cross section. The principal axis of the cylinder is the flow axis 14 in the channel 1. Perpendicularly to the flow axis 14, the cross section of the channel 1 is defined by a height denoted h and a width denoted L. The height h corresponds to the minimum dimension of the cross section (it is also the distance between the support 16 and the bottom of the recess of the structure 15), and the width L corresponds to the dimension in the direction orthogonal to that of the height.

In general, during use, the height h corresponds to the vertical, while the width L and the flow axis 14 are in the horizontal plane.

The value of h can be chosen as a function of the size of the molecules or deformable objects to be separated. In general, it is necessary that the shear according to the height of the channel 1 has an effect on the molecule or the deformable object, which requires that the dimension of the molecules or deformable objects in the liquid medium used is not less than the height of the channel 1 by a factor of more than 200 or 100 or 50 or 20.

At the two ends of the channel 1 there are provided a first reservoir 4 and a second reservoir 6 respectively. The reservoirs 4, 6 are provided with respective pressure control means 13a, 13b. Electrodes 10a, 10b are immersed in the reservoirs 4, 6 in order to allow an electric field to be generated in the channel 1.

An additional channel 2 cuts the channel 1 (perpendicularly or not). The additional channel 2 is formed in the same manner as the channel 1. The intersection between the channel 1 and the additional channel 2 defines the introduction zone 9.

The additional channel 2 is also provided with a first reservoir 3 and a second reservoir 5 at its ends. The reservoirs 3, 5 are provided with respective pressure control means 12a, 12b. Optionally, the reservoirs 3, 5 are also provided with respective electrodes 11a, 11b adapted to generate an electric field in the additional channel 2.

During use, the channel 1 and the additional channel 2 are filled with a solution, which is suitable for electrophoresis. A sample of molecules or deformable objects to be analysed is introduced into the device through the first reservoir 3 of the additional channel 2. By means of a hydrodynamic flow generated in the additional channel 2 and/or by means of an electric field generated in the additional channel 2, the molecules or deformable objects to be analysed migrate along the additional channel in the direction towards the second reservoir 5, as far as the introduction zone 9.

This first migration step makes it possible to obtain a homogeneous concentration of molecules or deformable objects to be analysed in the introduction zone 9 before the start of the actual separation of the molecules or deformable objects present in that zone.

In a second stage, the migration is interrupted, and migration of the molecules or deformable objects to be analysed is then effected in the channel 1, along the flow axis 14, from the first reservoir 4 to the second reservoir 6. To that end, a hydrodynamic flow is generated in the channel 1 (especially by the pressure control means 13a, 13b of the first reservoir 4 and of the second reservoir 6).

Conjointly, an electric field is generated in the channel 1 by means of the electrodes 11a, 11 b in the respective reservoirs 4, 6. Preferably, the electric field is suitable for applying to the molecules or deformable objects to be separated an electrostatic force which tends to displace them in the opposite direction to the hydrodynamic flow. The direction of the electric field therefore depends on the sign of the overall charge of the molecules or deformable objects to be separated.

Figure 3:
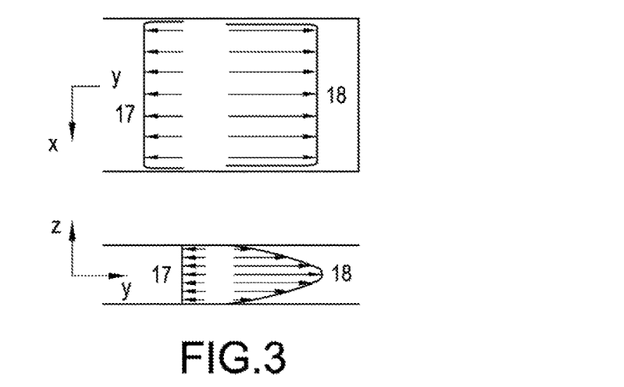
FIG. 3 is a schematic illustration of the hydrodynamic and electrophoretic force fields in the channel during the separation.

Referring to FIG. 3 (the top part of the figure being a top view and the bottom part a side view), during the separation, the electrophoretic force field 17 in the channel 1 during the separation is substantially uniform, both in the direction of the flow axis 14 (y axis) and according to the height h (z axis) and the width L (x axis) of the channel 1, except in the immediate vicinity of the walls of the channel (over a negligible characteristic length relative to the dimensions h and L).

With regard to the hydrodynamic force field 18, it is uniform in the direction of the flow axis 14 (y axis) and according to the width L (x axis), except in the immediate vicinity of the walls of the channel (over a negligible characteristic length relative to the dimension L). By contrast, it is not uniform according to the height h (z axis). Generally, it has a parabolic-type profile characteristic of Poiseuille's law.

The aspect ratio L/h of the channel 1 is chosen in order to obtain this configuration of the hydrodynamic force field: for that reason, the aspect ratio is generally greater than or equal to 10, or 15, or 20. The non-uniformity of the hydrodynamic force field 18 according to the height h is important for the effectiveness of the separation of the molecules or deformable objects. The uniformity thereof according to the width L makes it possible to avoid any loss of resolution, given that the detection is generally carried out, in the detection zone 8, in a given position (or over a given interval) along the flow axis and by summation of the signal along the width L.

The desired hydrodynamic flow profiles (characterised especially by given flow and average speed values) are obtained by actuating the respective pressure control means 13a, 13b (and optionally 12a, 12b) so as to generate a pressure difference between one or more inlet reservoirs and one or more outlet reservoirs. For example, in order to generate the hydrodynamic flow which ensures migration of the molecules or deformable objects to be separated from the introduction zone 9 to the detection zone 8, a pressure difference between the reservoirs 3, 4, 5 and the reservoir 6 is generated. For example, considering the geometry of the channels, a pressure difference of from 0.01 to 10 bar, preferably from 0.05 to 4 bar, and more particularly preferably from 0.1 to 1 bar, allows the desired hydrodynamic flow profiles to be obtained.

It is also possible to provide a system of valves to render the flows in the two channels 1, 2 independent of one another.

The detection means are not shown in the drawings. They can comprise a microscope objective on the side of the support 16 opposite the channel 1, and a detector connected thereto, such as a CCD camera. The individual molecules or the individual deformable objects can thus be detected on the acquired image, and an overall intensity measurement in the detection zone 8 or a portion thereof as a function of the time can be effected.

Means for analysing the measurements and presenting the data obtained can be associated with this device.

The device can also be integrated into a lab-on-a-chip, comprising, for example, other channels, reservoirs and/or electrodes similar to those described above. For example, the lab-on-a-chip can comprise a chemical or biochemical reaction device coupled, downstream, to the separating device according to the invention. Accordingly, implementation of the separation method according to the invention makes it possible to analyse the products of a chemical or biochemical reaction carried out in the lab-on-a-chip.

The lab-on-a-chip can also comprise means for collecting fractions corresponding to the different molecules or deformable objects which have been separated. These collecting means can be provided downstream of the detection zone 8. Alternatively, they can replace the detection zone 8, in which case the device is used solely for preparative purposes.

These collecting means can be provided in combination with the chemical or biochemical reaction device mentioned above, or without it.

EXAMPLES

The examples which follow illustrate the invention without limiting it.

Example 1—Separation of a Population of Double-Stranded DNA Molecules

In this example, the invention is carried out in order to effect the separation of a population of double-stranded DNA molecules having sizes of 500 bp, 1000 bp, 1500 bp, 2000 bp, 3000 bp, 4000 bp, 5000 bp, 6000 bp, 8000 bp and 10,000 bp.

The population of molecules is diluted in a buffer solution comprising 180 mM of trishydroxymethylaminomethane, 180 mM of boric acid, 4 mM of ethylenediaminetetraacetic acid, 0.5 µM of dithiothreitol and 2% by mass of polyvinylpyrrolidone (PVP, 360 kDa), with a total concentration of nucleic bases of 5 ng/µl, which corresponds for each of the sizes under consideration to respective molar concentrations of $5 \times 10^{-12}$ M (500 bp), $1.3 \times 10^{-12}$ M (1000 bp), $4.8 \times 10^{-13}$ M (1500 bp), $3.6 \times 10^{-13}$ M (2000 bp), $4.2 \times 10^{-13}$ M (3000 bp), $6.3 \times 10^{-14}$ M (4000 bp), $5.1 \times 10^{-14}$ M (5000 bp), $4.2 \times 10^{-14}$ M (6000 bp), $2 \times 10^{-14}$ M (8000 bp), $1.3 \times 10^{-14}$ M (10,000 bp).

The nucleic acids are made fluorescent by labelling with an intercalating agent (YOYO®, Molecular Probes) at a rate of one probe for 4 base pairs.

The device used for separating and analysing this population of molecules is as shown in FIG. 1. The channel 1 and the additional channel 2 have a width of 100 µm and a height of 2 µm. The introduction zone 9 and the detection zone 8 are separated by 5 mm.

200 µl of buffer solution not containing biological sample are arranged in the reservoirs 3, 4, 5 and 6 of the channel 1 of the additional channel 2. A flow of solution from the reservoirs 3, 4, 5 towards the reservoir 6 is created by adjusting the pressures in order to permit saturation of the surfaces with PVP, for a period of 30 minutes. 200 µl of solution containing the sample of interest are then arranged in the first reservoir 3 of the additional channel 2.

A plurality of migration tests are carried out by adjusting the potential difference and the pressure difference in the channel 1 to a plurality of different values ranging from 0 to 40 V and from 200 to 700 mbar, respectively.

Monitoring of the intensity in the detection zone 8 is carried out with the aid of a fluorescence microscope (100× magnification) and imaged with the aid of a CCD camera at a frequency of 5 Hz.

The best resolution over the whole of the range 500 to 10,000 bp is obtained with 20 V and 200 mbar, or 30 V and 500 mbar (the latter configuration additionally ensuring a migration time of less than 8 minutes).

Figure 4:
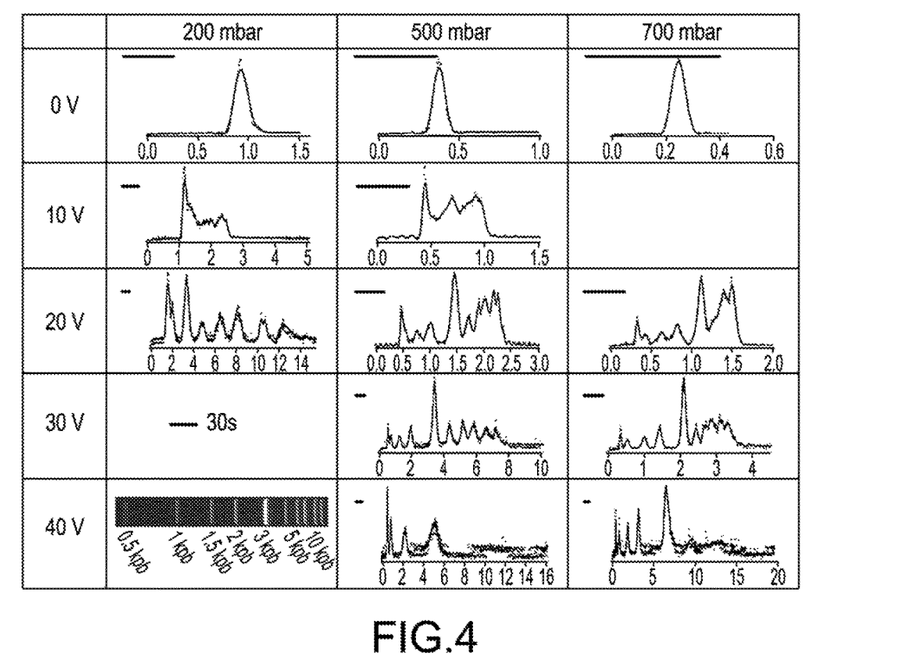
FIG. 4 shows results of the separation of DNA molecules ranging from 500 to 10,000 bp using the method of the invention, for various electric field and hydrodynamic flow conditions (see example 1 below). The x axis shows the time since the start of the migration (in minutes), and the y axis shows the light intensity received by the detector. A separation of the tested DNA population by conventional gel electrophoresis is also shown on the bottom left for comparison.
Figure 5:
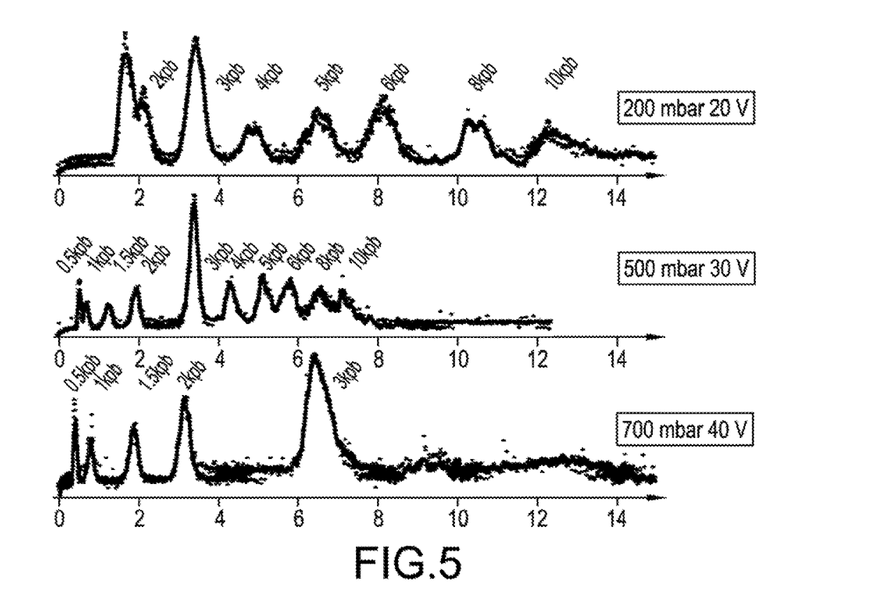
FIG. 5 shows in greater detail three of the separations presented in FIG. 4.
Figure 6:
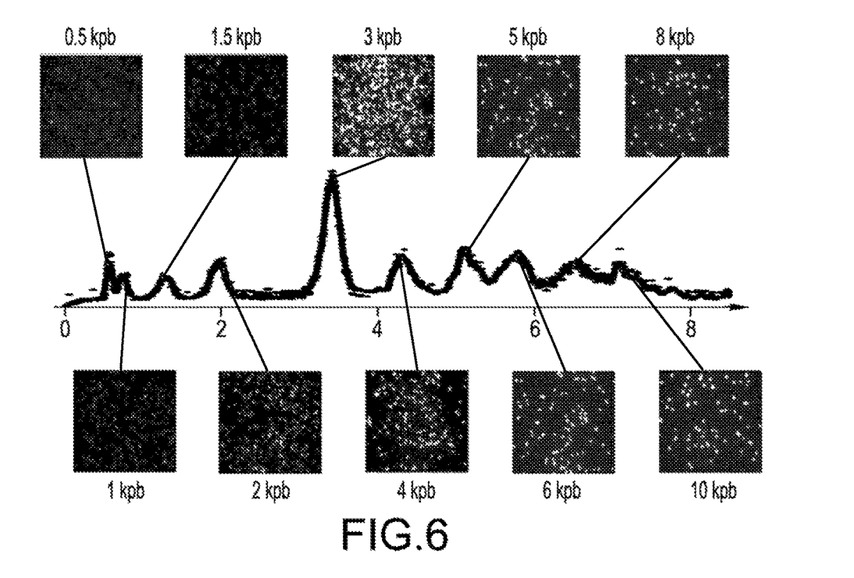
FIG. 6 again shows one of those separations (500 mbar and 30 V), as well as the images acquired for each of the intensity maxima, showing the possibility of visualisation of individual molecules.

The results are shown in FIGS. 4 to 6.

Example 2—Description of the Mechanism of Separation by Monitoring Single Molecules In this example, the same experimental device as in the preceding example is used. The migration of a DNA of approximately 48,000 base pairs (phage lambda DNA) in the channel is studied. The concentration by mass of polyvinylpyrrolidone (PVP, 360 kDa) is 2%. In a first stage, a pressure difference of 100 mbar is applied, and migrations are carried out with potential differences of 0, 5, 10, 15 and 20 V. The velocity of a large number of individual fluorescent DNA molecules is measured for each of these potential differences, and the velocity distribution is studied.

Figure 7:
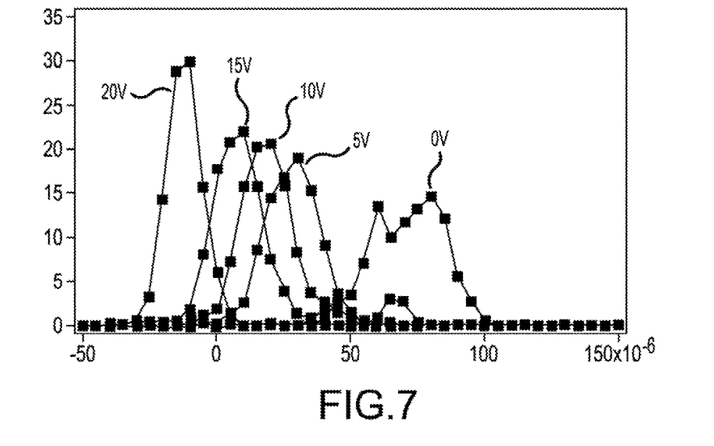
FIG. 7 is a diagram showing the distribution of the velocity of individual DNA molecules of 48,000 bp with various potential differences (shown in the figure) and a fixed pressure difference of 100 mbar (see example 2). The velocity of the molecules is indicated on the x axis in µm/s, and the percentage of events is shown on the y axis.

The results are shown in FIG. 7.

It is found that the dispersion of the velocity decreases when the potential difference increases, which is evidence of an effect of spatial localisation of the DNA molecules in the channel.

In a second stage, the distribution of the DNA molecules in the direction of the height of the channel is analysed. To that end, fluorescence intensity measurements are carried out in various focal planes, by means of the piezoelectric locator of the objective. The results are shown in the left-hand part of FIG. 8.

Figure 8:
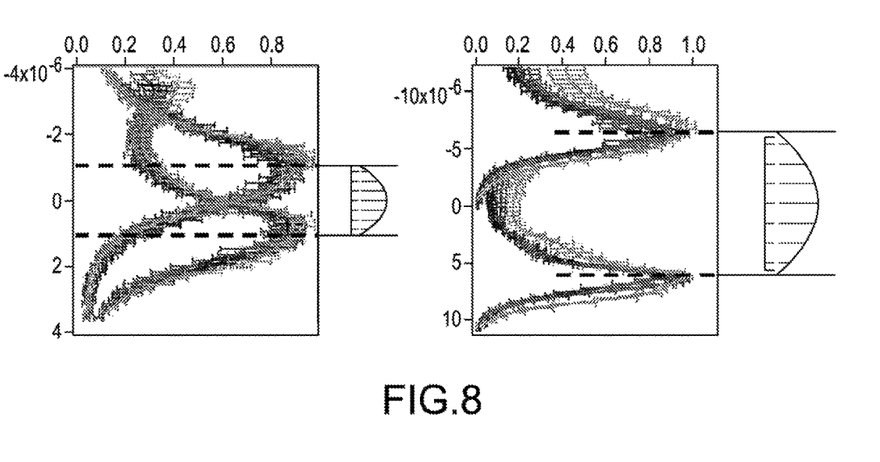
FIG. 8 is a diagram showing the spatial distribution of fluorescent DNA molecules of 48,000 bp in a channel having a height of 2 µm (left-hand part) and in a channel having a height of 12 µm (right-hand part), as explained in example 2. The altitude in µm is shown on the y axis (an altitude of 0 corresponding to the centre of the channel) and the measured light intensity (in arbitrary units) is shown on the x axis. The position of the walls of the channel is shown by dashed lines. The results obtained with different migration conditions, namely:
  for the channel having a height of 2 µm, potential difference/pressure difference pairs of 15.4 V/50 mbar; 23.5 V/120 mbar; 29.4 V/200 mbar; and 45 V/600 mbar;
  for the channel having a height of 12 µm, potential difference/pressure difference pairs of 15 V/10 mbar; 59 V/50 mbar; 83 V/100 mbar; and 114 V/200 mbar, have been superposed on the two parts of the diagram.

Four pairs of pressure difference and potential difference conditions were used, allowing a migration velocity (according to the axis of the channel) of the DNA molecules of substantially zero to be obtained. These pairs of conditions are as follows: 15.4 V/50 mbar; 23.5 V/120 mbar; 29.4 V/200 mbar; and 45 V/600 mbar. The four corresponding light intensity curves overlap approximately, and show that the DNA molecules are concentrated in the vicinity of the walls.

The experiment is then repeated with a device having a greater channel height, of 12 µm. The results are shown in the right-hand part of FIG. 8. The pairs of conditions used which allow the migration speed of the molecules along the channel to be cancelled out are as follows: 15 V/10 mbar; 59 V/50 mbar; 83 V/100 mbar; and 114 V/200 mbar. It is again found that the DNA molecules are located in the vicinity of the walls of the channel.

Example 3—Influence of the Nature of the Liquid Medium

In this example, the same experimental device as in example 1 is used, and the separation of the same DNA population is studied. The influence of the non-Newtonian character of the liquid medium on the effectiveness of the separation is tested.

To that end, migrations are carried out by varying the concentration of PVP in the buffer solution between values of 0.1%, 2% (as in example 1) and 4%.

At a concentration of 0.1%, the medium is a Newtonian fluid. At concentrations of 2 and 4%, it is a non-Newtonian fluid.

Figure 9:
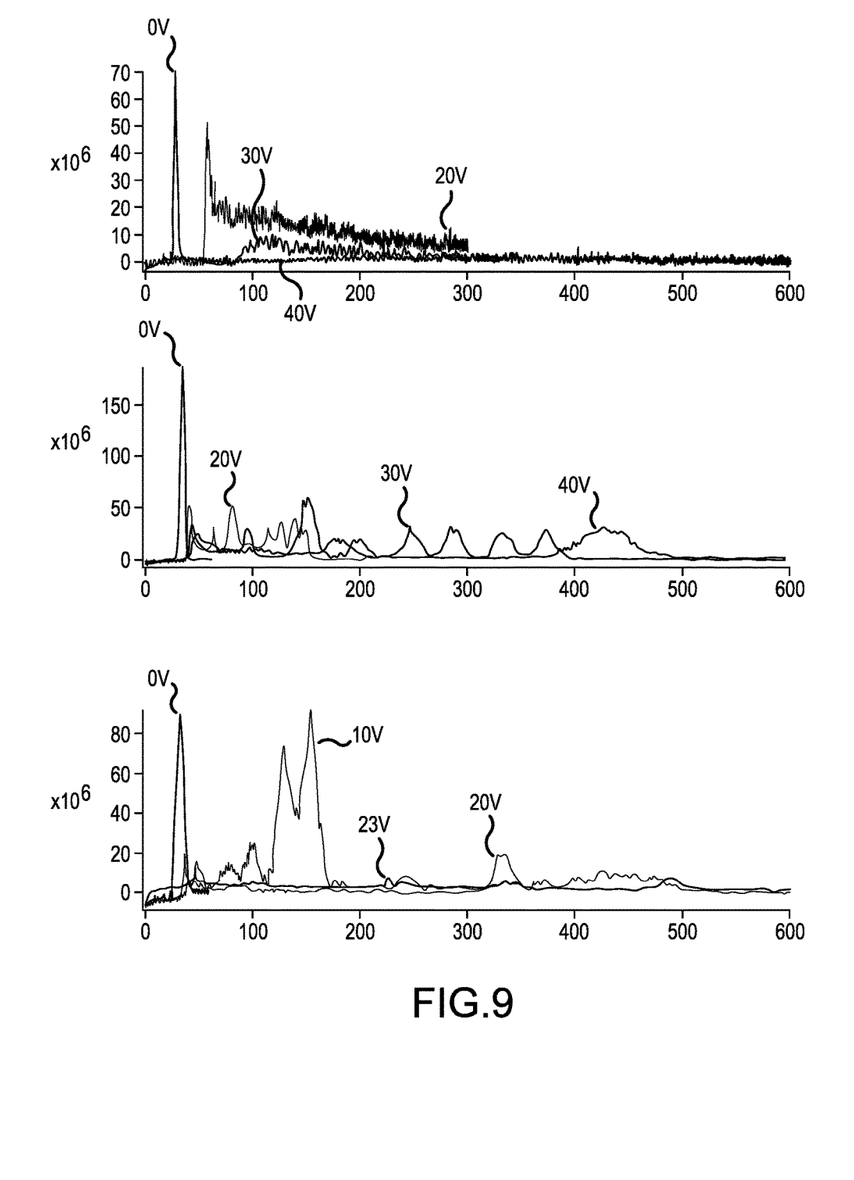
FIG. 9 shows results of the separation of DNA molecules ranging from 500 to 10,000 bp using the method of the invention, for various electric field and polyvinylpyrrolidone (PVP) concentration conditions in the medium (see example 3 below). The x axis shows the time since the start of the migration (in seconds), and the y axis shows the light intensity received by the detector. The top graph is obtained with 0.1% PVP, the middle graph with 2% PVP, and the bottom graph with 4% PVP.

The pressure difference applied is 50 mbar, 150 mbar and 600 mbar for the respective PVP concentrations of 0.1%, 2% and 4%. The potential differences applied are 0, 10, 20, 23, 30 and 40 V, according to the experiments. The results are shown in FIG. 9. It is found that the separation is greatly improved when the separation medium comprises a PVP concentration greater than a certain threshold, close to the coverage concentration of 0.4% of the PVP (340 kDa), conferring non-Newtonian properties on the liquid separation medium.

These non-Newtonian properties are demonstrated with dynamic mechanical analysis methods using a Couette rheometer.

More precisely, the fluid is arranged between a central cylinder of radius R and a peripheral cylinder (the distance between the two cylinders being denoted ΔR and the height of the cylinders being denoted h). The central cylinder is made to rotate with a frequency of rotation w (in s$^{-1}$) and the mechanical moment M induced on the peripheral cylinder is measured. The stress is determined as being $\sigma=M/(2\pi R^2 h)$. The shear rate is defined as being $\tau=R \cdot w/\Delta R$.

When a rotation of the cylinder that is variable over time is applied, according to a sinusoidal-type function, it is practical to represent the stress and the shear rate as a function of time by complex numbers: $\sigma(t)=\sigma_0(w) \cdot e^{iwt}$ and $\tau(t)=\gamma(w) \cdot e^{i(wt+\varphi)}$. This makes it possible to define a complex viscosity of the fluid $\mu(w)=\mu'(w)-i \cdot \mu''(w)$, where $\mu'(w)$ and $\mu''(w)$ denote real numbers, and $\sigma(t)=\mu(w) \cdot \tau(t)$. There are additionally defined the moduli of elasticity $G'(w)=w \cdot \mu''(w)$ (storage modulus) and $G''(w)=w \cdot \mu'(w)$ (loss modulus).

In the case of a Newtonian fluid, $G'(w)=0$ and $G''(w)=w \cdot \mu_0$, $\mu_0$ being the (constant) viscosity of the fluid.

Figure 10:
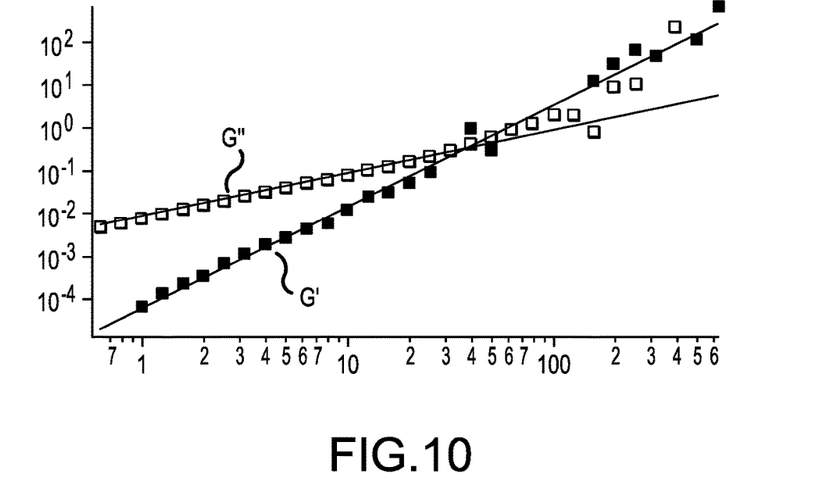
FIGS. 10 and 11 show the rheological behaviour of a solution comprising 2% PVP.
Figure 11:
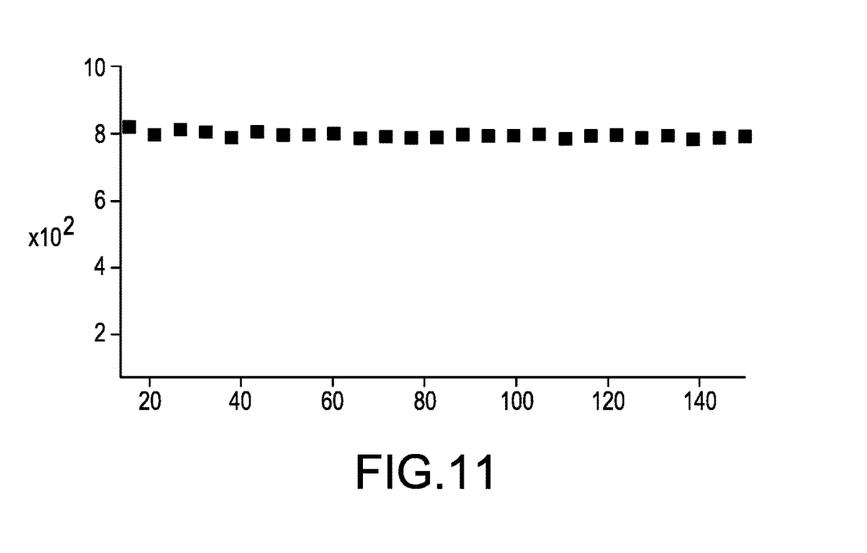

By contrast, the solution comprising 2% PVP has a non-zero component $G'(w)$ which becomes dominant at high frequencies (above about 30 Hz) (FIG. 10). The viscosity, on the other hand, is constant when the shear rate varies, under steady-state conditions (FIG. 11).

The invention claimed is:

1. Method for separating a plurality of deformable objects in a liquid medium, comprising:
    introducing the deformable objects into a single channel from an additional channel, wherein an intersection between the single channel and the additional channel defines an introduction zone, in order to obtain a homogeneous concentration of deformable objects in the introduction zone, the single channel having a flow axis and a cross section orthogonal to the flow axis, and the minimum dimension of said cross section being less than or equal to 200 µm; and
    applying a hydrodynamic flow with a parabolic profile characteristic in said single channel together with the application of an electric field in said single channel, allowing the deformable objects to be displaced in the single channel according to the flow axis and to be separated along the flow axis,
    wherein the liquid medium is non-Newtonian fluid.

2. Method according to claim 1, wherein the introduction of the deformable objects is carried out in the introduction zone of the single channel, and the displacement of the deformable objects is carried out from the introduction zone to a detection zone of the single channel, the method further comprising:
    detecting deformable objects which arrive in the detection zone.

3. Method according to claim 1, wherein:
    the minimum dimension of the single channel is less than or equal to 25 µm; and/or
    the ratio between the minimum dimension of the cross section and the dimension of the cross section in a direction orthogonal to that of the minimum dimension is less than or equal to 1/10; and/or
    the distance between the introduction zone and the detection zone of the single channel is from 500 µm to 20 cm.

4. Method according to claim 1, wherein the liquid medium comprises uncharged polymers.

5. Method according to claim 4, wherein the concentration of uncharged polymers is greater than or equal to the concentration from which the polymers are in contact.

6. Method according to claim 4, wherein the uncharged polymers are chosen from polyvinylpyrrolidone, poly(ethylene glycol), polyacrylamide and mixtures thereof.

7. Method according to claim 1, wherein the deformable objects have a modulus of elasticity less than or equal to $10^9$ Pa.

8. Method according to claim 1, wherein the deformable objects are chosen from molecules such as nucleic acid molecules, supramolecular assemblies, cells and fragments of cells.

* * * * *